United States Patent
Miller et al.

(10) Patent No.: US 7,321,052 B2
(45) Date of Patent: Jan. 22, 2008

(54) PROCESS FOR PRODUCTION OF A COMPOSITION USEFUL AS A FUEL

(75) Inventors: Dennis J. Miller, Okemos, MI (US); Lars Peereboom, Haslett, MI (US); Aspi K. Kolah, East Lansing, MI (US); Navinchandra S. Asthana, East Lansing, MI (US); Carl T. Lira, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 24 days.

(21) Appl. No.: 11/364,241

(22) Filed: Feb. 28, 2006

(65) Prior Publication Data

US 2006/0199970 A1    Sep. 7, 2006

Related U.S. Application Data

(60) Provisional application No. 60/657,580, filed on Mar. 1, 2005.

(51) Int. Cl.
| C07C 69/02 | (2006.01) |
| C07C 43/00 | (2006.01) |
| C07D 317/70 | (2006.01) |
| C07D 319/06 | (2006.01) |

(52) U.S. Cl. ............ 560/231; 568/590; 549/369; 549/430

(58) Field of Classification Search ............ 560/129, 560/190, 193, 198, 234, 238
See application file for complete search history.

(56) References Cited

U.S. PATENT DOCUMENTS

| 5,917,059 | A | 6/1999 | Bruchmann et al. |
| 6,548,681 | B1 | 4/2003 | Chopade et al. |
| 6,713,640 | B2 | 3/2004 | Miller et al. |
| 6,890,364 | B2 | 5/2005 | Delfort et al. |
| 2003/0167681 | A1* | 9/2003 | Delgado ............ 44/388 |
| 2004/0025417 | A1* | 2/2004 | Delfort et al. ......... 44/349 |

* cited by examiner

Primary Examiner—Karl Puttlitz
(74) Attorney, Agent, or Firm—Ian C. McLeod

(57) ABSTRACT

A process for the preparation of a fuel oil (diesel fuel or heating oil) composition which is a mixture of an alkanol tranesterified fatty acid ester triglyceride and an acetal of glycerol is described. The process preferably provides a prestep of the formation of at least some of the alkanol transesterified triglyceride containing the glycerol for use in the formation of the acetal of glycerol. The composition can also be formed from a reaction of 1,1-dimethoxy- or 1,1-diethoxyethane and glycerol to form the acetal in the alkanol transesterified triglyceride.

15 Claims, 4 Drawing Sheets

PROCESS FOR PRODUCTION OF A COMPOSITION USEFUL AS A FUEL

CROSS-REFERENCE TO RELATED APPLICATIONS

This application claims priority to Provisional Patent Application Ser. No. 60/657,580, filed Mar. 1, 2005.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to a process for the preparation of a composition comprising a mixture useful as a diesel fuel or fuel oil. In particular, the present invention relates to a process which enables production of the composition without the need for an intermediate separation (extraction) step to remove a glycerol by-product from transesterification of a triglyceride, such as vegetable oil.

(2) Description of the Related Art

Biodiesel is rapidly gaining momentum as the next major biofuel for energy sustainability. Biodiesel production in Europe is already on the order of one billion gallons annually, but U.S. production is only 100 million gallons per year. However, the recent spike in petroleum prices, the increasing environmental awareness of U.S. consumers, and the October, 2004 passage of the biodiesel tax incentive (H.R. 4520) by Congress, providing a $1.00 per gallon tax credit for biodiesel, are all spurring interest and rapid growth in biodiesel technologies in the U.S.

Nearly all biodiesel production from vegetable oil (triglyceride) follows a common set of reaction pathways: first, tranesterification of the triglyceride with excess methanol and NaOH catalyst to give fatty acid ester, which is the biodiesel product; then separation of the ester (+residual oil) liquid phase from the byproduct glycerol (+NaOH) phase; distillation to separate the ester from residual oil; and recovery of pure glycerol as a byproduct. The resulting methyl ester is marketed as an additive to fuel in the U.S., usually about 2% to 20% by volume, and so that the resulting composition is called "biodiesel". There are oxygenates that can be added to the diesel fuel to promote cleaner burning as well. The uncertainty of a market for large quantities of glycerol from biodiesel and the need for continuous biodiesel production processes are two recognized challenges for large- scale biodiesel implementation.

U.S. Pat. No. 6,890,364 B2 and US2004/0025417 A1 to Delfort et al describe a process for producing glycerol acetals for use in diesel fuels, and they are incorporated herein by reference in their entireties. U.S. published application 2003/0167681 A1, which is also incorporated by reference in its entirety, describes a similar two step process. The process conditions enable the formation of the acetals, with filtration of the solid and catalyst from the composition produced, which is a mixture of acetals. The acetal mixture is added in an amount between 1 to 40%, preferably 1 to 20% by volume to diesel fuel and is soluble in the heating or diesel fuel oils which is important for preventing separation on storage. The acetal additive reduces particulate emissions, particularly from diesel engines and functions like an oxygenate.

U.S. Pat. No. 5,917,059 to Bruchmann relates to a process for forming acetals. Also U.S. Pat. Nos. 6,713,640 and 6,548,681 to Miller et al relate to a process for preparing acetals. Both references are incorporated herein by reference in their entireties.

There is a need for a more direct process for the formation of such glycerol acetals in fuel oil compositions.

OBJECTS

It is therefore an object of the present invention to provide a process for the preparation of an oil (diesel or heating) which bypasses the need for a separation step, usually a distillation step, after the transesterification formation of the alkanol ester of the triglyceride, to remove glycerol. It is further an object of the present invention to provide a process which reliably and economically produces biologically derived fatty acid esters for use in fuel oils, such as heating oil or biodiesel. These and other objects will become increasingly apparent by reference to the following description and the claims.

SUMMARY OF THE INVENTION

The present invention relates to a process for the preparation of a composition useful as a fuel oil which comprises reacting in a closed vessel a mixture comprising glycerol and a lower alkanol transesterified fatty acid ester, wherein the alkanol contains 1 to 6 carbon atoms, with an aldehyde or ketone containing 1 to 20 carbon atoms or a diether containing 2 to 20 carbon atoms, in the presence of a solid acid catalyst in a closed vessel at an elevated temperature to form a mixture of the transesterified fatty acid ester and the acetal of the glycerol to provide the composition.

The present invention relates to a process for the preparation of a composition useful as a fuel oil which comprises:
reacting in a closed vessel a mixture resulting from partial transesterification of a triglyceride with a lower alkanol containing 1 to 6 carbon atoms, the mixture comprising glycerol, monoglycerides, diglycerides, triglycerides, lower alkanol transesterified fatty acid esters, and excess alkanol, with an aldehyde, ketone or diether containing 1 to 20 carbon atoms as a glycerol acetal forming agent in the presence of a solid acid catalyst in a closed vessel at an elevated temperature to form a mixture of the fatty acid ester and the acetal of the glycerol to provide the composition. Preferably the acetal forming agent is acetaldehyde. Preferably the lower alkanol transesterified fatty acid ester is a methyl or ethyl ester derived from a methanol or ethanol transesterification of a vegetable oil triglyceride. Preferably the aldehyde is acetaldehyde. Preferably the process is continuous. Preferably the process comprises a prestep of partial transesterification of a triglyceride with the alkanol to provide the mixture. Preferably the process with the prestep is continuous. Preferably the catalyst used is a solid acid catalyst. Preferably the process comprises the step of adding the alkanol to the mixture to react with unreacted triglycerides present in the mixture. Preferably the process is performed as a continuous reactive distillation with removal of the composition as it is formed. Preferably the mixture with fatty acid ester further comprises impurity amounts of free fatty acids and water.

The present invention also relates to a process for the preparation of a composition useful as a fuel oil which comprises reacting a mixture comprising 1,1-dimethoxyethane or 1,1-diethoxyethane with glycerol in a lower alcohol transesterified fatty acid ester or in the mixture described above, wherein the alkanol contains 1 to 6 carbon atoms, in the presence of a solid acid catalyst in a closed vessel, at an elevated temperature to form a mixture of the fatty acid ester and an acetal of the glycerol to provide the composition. Preferably the process comprises a further prestep of reacting a mixture of acetaldehyde and methanol or ethanol to form the 1,1-dimethoxyethane or 1,1-diethoxyethane and then removing water formed in the reaction from the mixture. Preferably methanol or ethanol are separated from the mixture. Preferably the reaction is conducted at a pressure between about 1 atmosphere and 27.2 atmosphere (400 psig) and at a temperature between about 800 and 200° C.

The present invention also relates to a process for the preparation of a composition useful as a fuel from a transesterified fatty acid ester, the improvement which comprises:

(a) reacting methanol or ethanol with acetaldehyde to form a 1,1-di-methoxyethane or 1,1-diethoxyethane and water in a reaction mixture;

(b) separating water from the reaction mixture; and reacting the reaction mixture of step (b) with glycerol in the transesterified fatty acid ester from the transesterification to form a mixture of 2-methyl-4-hydroxymethyl 1,3-dioxolane and 5-hydroxymethyl-2-methyl-1,3-dioxane in the transesterified fatty acid ester as the composition. Preferably the mole ratio of methanol or ethanol to acetaldehyde in step (a) is between about 1 to 1 and 4 to 1.

It is well known that methanol is the alcohol most used currently to make biodiesel via a base-catalyzed, batch process. This is because methanol is inexpensive; however, methanol is advantageous from a batch processing standpoint in that it does not dissolve biodiesel or glycerol well, and thus two liquid phases are formed as reaction progresses. The batch process takes advantage of these two phases in that they offer an economical means of separating biodiesel from byproduct glycerol at the end of reaction. In the present continuous process, which involves a fixed-bed reactor and a reactive distillation column, it is desirable to maintain a single reaction phase such that all reactants can achieve intimate contact: with each other. Ethanol is a substantially better solvent than methanol for glycerol and biodiesel, such that in a relatively small excess of ethanol only a single reaction phase is present. This single phase leads to much more efficient operation in the continuous process—hence ethanol is a preferred alcohol from a processing standpoint.

In addition to achieving better solubilities, ethanol is a desirable component to include in biodiesel. The fatty acid ethyl esters (FAEE) that constitute "ethyl" biodiesel have better fuel properties than fatty acid methyl esters of traditional biodiesel. Ethanol is a "green" fuel, as it is derived from renewable feedstocks such as corn and biomass. Ethanol may have better long-term price stability than methanol, which is desired from natural gas, because ethanol production processes from corn and biomass are still improving whereas natural gas prices are expected to trend even higher in the next several years. Finally, ethanol is less toxic than methanol, and diesel fuel can withstand the presence of low concentrations of ethanol (<5%) without adverse effects.

A schematic of acetal synthesis without producing water in the transestification reaction is as follows:

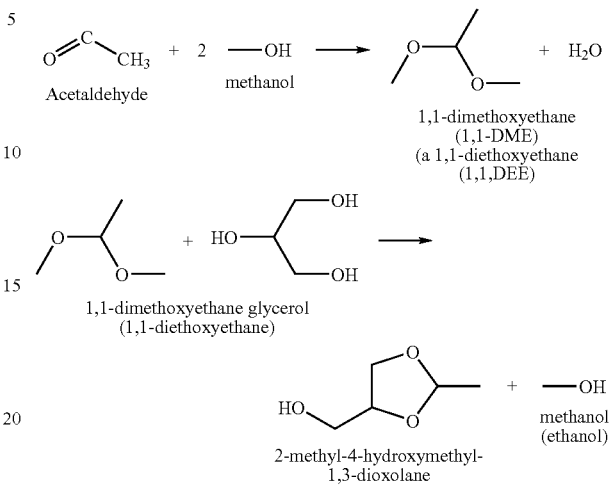

The six-membered ring compound 5-hydroxymethyl-2-methyl-1,3-dioxane is made in nearly equal quantities to the 2-methyl-4-hydroxymethyl-1,3-dioxolane shown above.

Acetal synthesis without producing water in reactive distillation is important in that water liberated in glycerol acetal formation could hydrolyze methyl esters and degrade solid acid catalysts. This can be avoided via the formation of intermediate 1,1-DME as acetal-producing species in a separate reaction vessel as a prestep. 1,1-DME (a 1,1-DEE) is then fed into the RD column, where it reacts with glycerol and liberates methanol (or ethanol).

BRIEF DESCRIPTION OF DRAWINGS

(FIG. 3 shows continuous biodiesel and glycerol acetal formation via 1,1-diethoxyethane (1,1-DEE) as acetalizing agent.)

DESCRIPTION OF THE PREFERRED EMBODIMENTS

The process for biodiesel production uses reactive distillation to completely convert vegetable oil to biodiesel or fuel and while simultaneously converting glycerol to an acetal derivative suitable for inclusion in biodiesel as a fuel additive. Formation and inclusion of this acetal glycerol derivative into biodiesel is important for several reasons: 1) it adds to the overall mass yield of fuel produced; 2) it removes glycerol as it is formed during transesterification, allowing that equilibrium-limited reaction to proceed to completion; and 3) it removes the necessity and liability of downstream recovery, purification and sale, or disposal of glycerol. Moreover, the proposed process uses solid acid catalysts such as ion exchange resins instead of soluble base, thus avoiding the cost of recovering and disposing of a base from the process.

The glycerol is preferably converted to its acetal derivative in situ after transesterification. The resulting glycerol acetal is thus a biodiesel fuel additive. Aldehydes or ketones readily react with vicinal diols in the presence of acid to form cyclic acetals; Scheme 1 shows the reaction of glycerol with acetaldehyde to form 4-hydroxymethyl-2-methyl-1,3-dioxolane (HMD) and byproduct water.

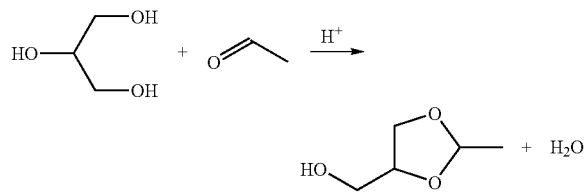

Scheme 1. Formation of Glycerol Acetal (HMD) from Glycerol and Acetaldehyde.

Reaction of acetaldehyde with glycerol also forms the six-member cyclic acetal (5-hydroxymethyl-2-methyl-1,3-dioxane) via the C1 and C3 glycerol hydroxyl groups, so the final HMD product is a mixture of isomers. The acetal products are volatile (b.p. 180-200° C.) compounds with good combustion properties. Any aldehyde or ketone can be used, but acetaldehyde is a preferred reactant because it can be readily and reproducibly made by catalytic oxidation of ethanol. Delfort et al (cited previously) has recently reported that addition of 5 wt % glycerol acetal mixtures (HMD) to diesel fuel improves diesel fuel performance, with particulate emissions lowered by 10-30%. Thus, HMD is a good fuel additive for inclusion in the final biodiesel product.

Figure 1:
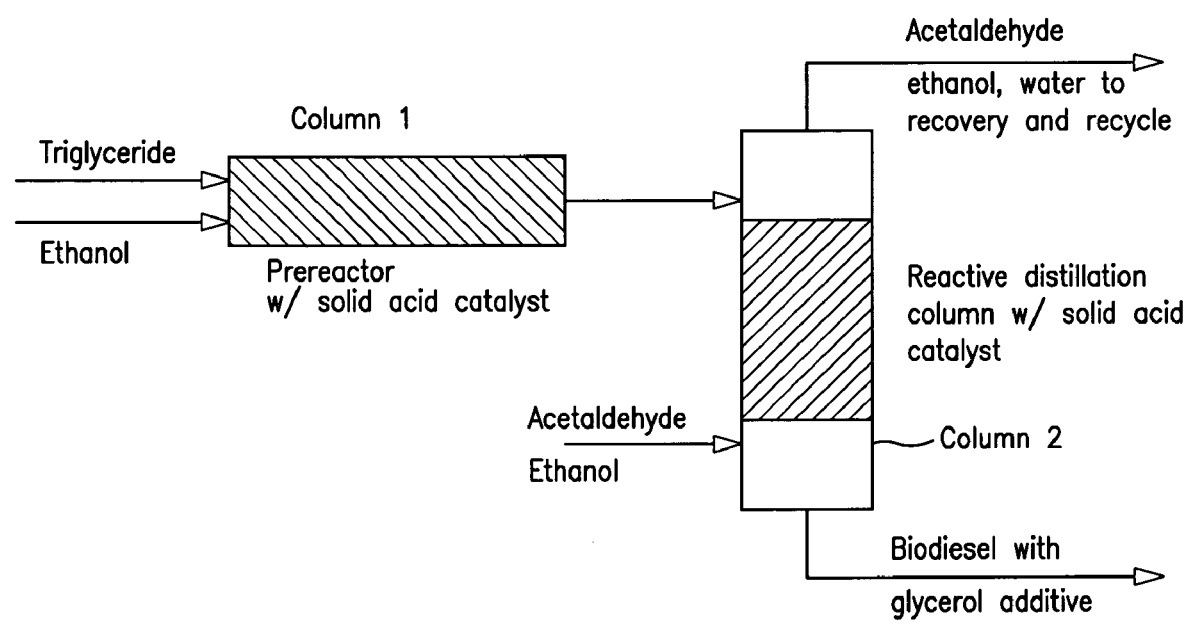
FIG. 1 is a schematic flow diagram of a process for the preparation of the composition of the present invention which is preferably a mixture of glycerol acetals, of acetaldehyde and a pre-reactor produced ethanol transesterified triglyceride.

The process is shown in FIG. 1. Vegetable oil is first partially converted via transesterification in a continuous prereactor (fixed bed, stirred, bubble or other multiphase configuration) containing a solid acid catalyst. Either ethanol or methanol, or a mixture of the two, can be effectively used as the alcohol feed; methanol is cheaper, but ethanol better solubilizes all species into a single phase.

Because transesterification is an equilibrium-limited reaction, the prereactor column 1 effluent stream is a mixture of biodiesel, unreacted oil, glycerol, and alcohol. This stream is fed to the top of a continuous, countercurrent flow reactive distillation column 2. A mixture of alcohol and acetaldehyde are fed near the bottom of the column. Reactive distillation columns usually contain three sections or zones, an enriching zone to purify the top product, a reactive zone containing the solid catalyst in which reactions take place, and a stripping zone to purify the bottoms product. With the reactive zone of the column operating near 80° C. to 200° C. preferably 130° C. to 160° C., the volatile alcohol, aldehyde, and any water present move upward in the column as vapors, while the ester, oil, and glycerol move downward as liquids. In the reactive zone, the alcohol contacts unreacted or partially reacted triglycerides such that further transesterification to fatty acid ester takes place. Simultaneously, acetaldehyde reacts with glycerol to form the acetal derivatives, with product water entering the vapor phase and exiting the top of the column away from the biodiesel product. Thus, as the liquid phase moves downward in the column, glycerol is converted to HMD and removed as a product of transesterification, allowing the equilibrium biodiesel formation reaction to proceed to completion.

Pure biodiesel and HMD exit the bottom of the column with no further purification necessary. Water, alcohol, and acetaldehyde exit the top of the column, where unreacted acetaldehyde and alcohol are recovered and recycled via simple distillation.

Figure 2:
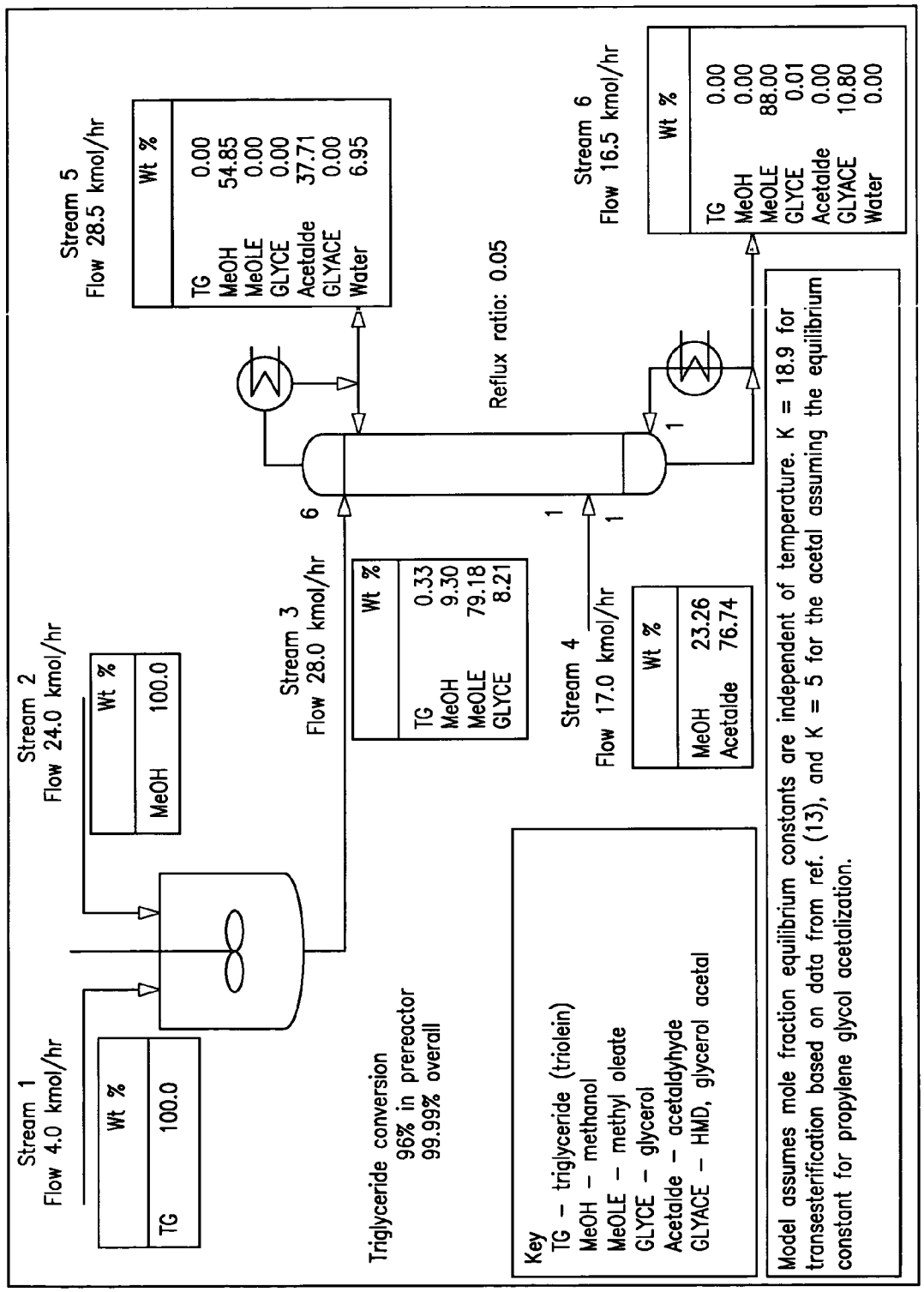
FIG. 2 is a schematic flow diagram showing large scale computer modeled mass balance results from the process of FIG. 1 based upon established parameters of Dhale et al, Chem. Engineering Science 2881-2890 (2004)).

FIG. 2 shows the result of a process simulation using AspenPlus process simulation software. The simulation has been conducted by accounting for only the equilibrium phase and reaction behavior among the species in the system. It thus tests the thermodynamic feasibility of the proposed process. Two reactors are simulated—a prereactor where the feed to the process is partially converted to biodiesel, and second the reactive distillation column wherein the completion of transesterification takes place and formation of the glycerol acetals take place.

Stream 1 (triglyceride—in this case triolein, a model triglyceride) and Stream 2 (methanol) are mixed in the stirred prereactor to give 96% conversion of triglycerides and an exit Stream 3 containing small quantities of unreacted triglycerides. Stream 3 is fed to the reactive distillation column along with Stream 4, a combination of methanol and acetaldehyde. In the 15 stage column, complete conversion of triglycerides is achieved along with almost complete conversion of glycerol to the desired glycerol acetal compounds.

The results depicted in FIG. 2 indicate that the thermodynamics of the continuous biodiesel process are favorable and thus that the process is feasible from a thermodynamic viewpoint. The numbers next to the distillation column in FIG. 2 are the stage numbers for feeding and withdrawing streams from the column—it can be readily observed that only a small column (15 stages) is required to complete biodiesel formation.

Economic Aspects of the Proposed Process

Formation of HMD and its inclusion in biodiesel incurs additional cost to supply acetaldehyde, to recycle acetaldehyde and ethanol, and to remove water. These costs are offset by the alleviation of glycerol and catalyst recovery costs, by the raw catalyst cost, and by the expanded biodiesel yield realized by HMD formation. Acetaldehyde can be purchased on the spot market (the worst-case scenario) at $0.455/lb; approximately 0.5 lb acetaldehyde (MW=44) is required per lb glycerol (MW=92). Since byproduct glycerol is formed at 0.7 lb/gallon biodiesel, the acetaldehyde cost per gallon of biodiesel is $0.16 at stoichiometric consumption rates. With the molecular weight of fatty acid esters approximately 300, addition of HMD (MW=120) to biodiesel expands the yield by about 13%, or with biodiesel at $1.50 per gallon, HMD will add about $0.20/gallon in value. Thus, this shows that the cost of HMD formation is essentially offset by the additional value it brings in enhanced biodiesel yield. This does not include the savings realized by removing glycerol from the fuel oil and catalyst recovery from the process.

The broad invention is to form the acetal of glycerol, either the five-member or six-member ring, in a mixture with the alcohol transesterified fatty acid esters and then burn it along with the biodiesel. The acetal formation reaction nominally uses acetaldehyde to react with glycerol; indeed, that is a straightforward reaction that proceeds to near completion. The reaction of glycerol with acetaldehyde to form the cyclic acetal liberates water, and this water could be a problem in the biodiesel formation reactions in that hydrolysis of the fatty acid methyl esters that constitute biodiesel might take place to liberate the free fatty acids, which is undesirable. As discussed previously, as an alternative, acetaldehyde are reacted with methanol to form 1,1-dimethoxyethane ($CH_3$—CH—$(OCH_3)_2$). The reaction involves one mole of acetaldehyde and two moles of methanol to give the 1,1-dimethoxyethane and water. The water is separated easily from the product, as 1,1-dimethoxyethane boils at 64° C. Dimethoxyethane is also commercially available. The same reaction can be conducted with 2 moles of ethanol and 1 mole of acetaldehyde to form 1,1-diethoxyethane.

1,1-dimethoxyethane or 1,1-diethoxyethane is then reacted with glycerol to form the cyclic acetal and two moles of methanol in the reactive distillation setup. No water is formed as it is when acetaldehyde is used, so that the possible problem of biodiesel hydrolysis in the reactive distillation column because of the presence of water is alleviated. Also, 1,1-diethoxyethane can be used as well. It is made from acetaldehyde and two moles of ethanol.

Figure 3:
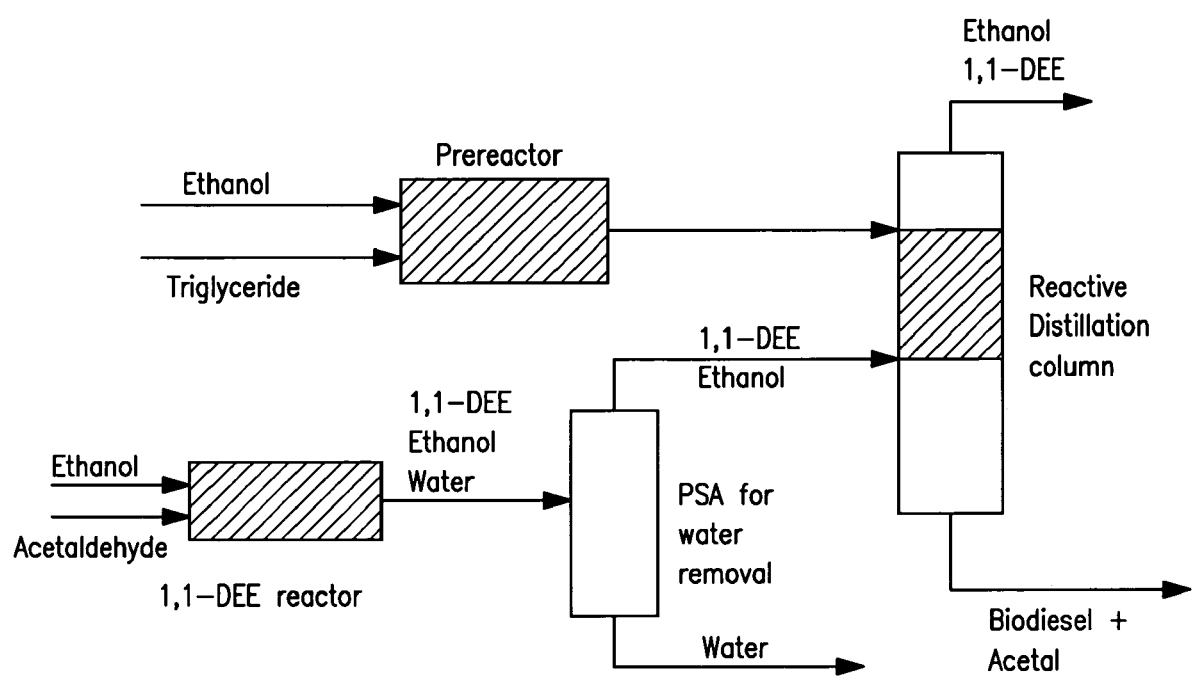
FIG. 3 is a schematic flow diagram showing a separate acetaldehyde and alcohol reaction vessel pre-step to form 1,1-dimethylethane or 1,1-diethylethane, which is reacted with the glycerol in a main reaction vessel.

FIG. 3 shows the process with the vessels for conducting the reactions. 1,1-DEE is formed via reaction of acetaldehyde with excess ethanol over an acid catalyst in 1,1-DEE reactor, where nearly complete conversion of acetaldehyde can be obtained. If complete acetaldehyde conversion is not achieved, unreacted acetaldehyde can readily be recovered from the exit stream of the 1,1-DEE reactor by distillation, because of its low boiling point (21° C.) and recycled back to the reactor feed. Water as a reaction product is removed from the 1,1-DEE reactor exit stream by methods standard to the industry such as pressure swing adsorption using 3A molecular sieves. 1,1-DEE and ethanol are then fed to the reactive distillation column where 1,1-DEE reacts with glycerol to form the glycerol acetals and ethanol. In this mode of operation, water is excluded from the reactive distillation column and thus possible hydrolysis of fatty acid esters (biodiesel) is avoided. Further, this mode of operation allows water-sensitive acid catalysts to be used in the reactive distillation column. With such water-sensitive catalysts, it is a required, standard practice to dry the triglyceride feedstock and feed ethanol prior to feeding them to the process.

Figure 4:
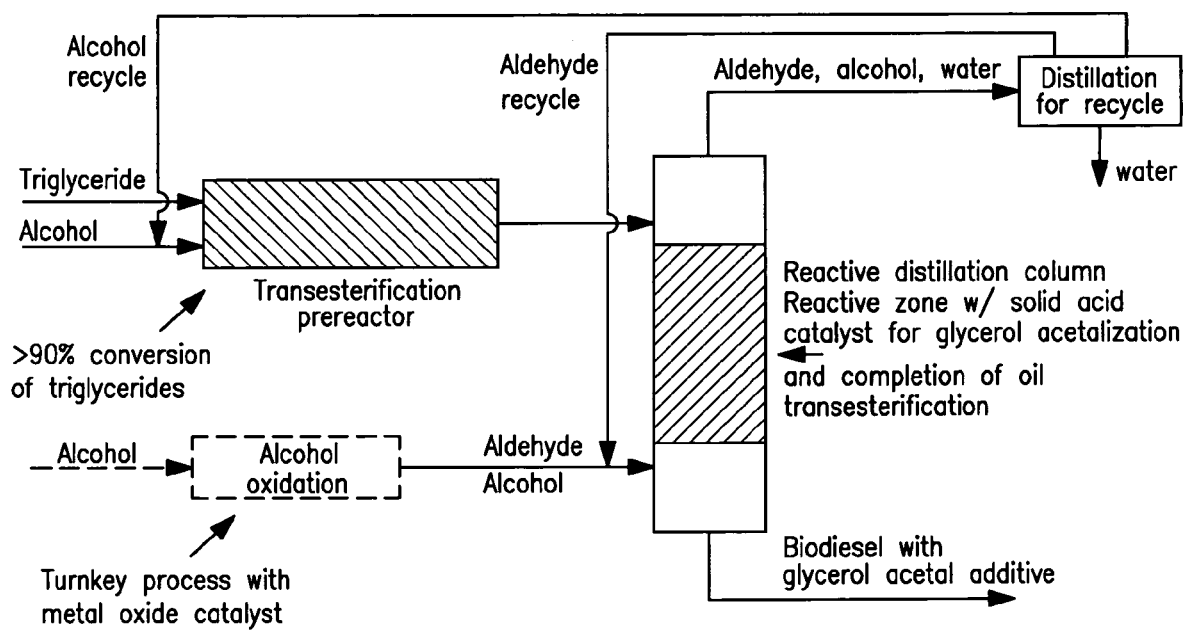
FIG. 4 is a schematic flow diagram, as a modification of FIG. 1, with a reactor vessel for oxidizing alcohol to the acetal. The partial oxidation of the alcohol to the aldehyde is an industrially practiced route to the aldehyde (acetaldehyde) formation.

In FIG. 4 a pre-reactor is used to form the acetaldehyde by a conventional reaction as discussed previously. The distillate stream from the reactive distillation column contains water, alcohol, and excess, unreacted acetaldehyde. This stream can be recovered and the components recycled back to the stream to give the most efficient operation of the process. Acetaldehyde is removed first by regular distillation or flash, and then ethanol and water are separated either using a dedicated ethanol-water separation system involving pressure swing adsorption with molecular sievers or by returning the mixture to the ethanol-water separator in an integrated ethanol production facility. The recycle of unused reactants in the process applies to all alternate concepts in the described invention. For example, when 1,1-DEE is used as the acetal forming agent as in FIG. 3, there are two components exiting the top of the distillation column, ethanol and 1,1-DEE. These two components can be separated by regular distillation and the individual components recycled to the process.

It is intended that the foregoing description be only illustrative of the present invention and that the present invention be limited only by the hereinafter appended claims.

We claim:

1. A continuous process for the preparation of a composition useful as a fuel oil which comprises:
   (a) reacting in a first closed vessel containing a first solid acid catalyst, a triglyceride and a lower alkanol containing 1 to 6 carbon atoms at a first elevated temperature to produce a first mixture comprising glycerol, monoglycerides, diglycerides and triglycerides, lower alkanol, and transesterified fatty acid ester as a partial transesterification mixture; and
   (b) reacting in a second closed vessel above a second acid catalyst the partial transesterification mixture and additional of the alkanol, with an aldehyde, ketone containing 1 to 20 carbon atoms or a diether containing 2 to 20 carbon atoms below the second acid catalyst at a second elevated temperature with removal of excess alkanol, and aldehyde, ketone or diether from an upper portion of the second vessel, to form a mixture of the transesterified fatty acid ester and a glycerol acetal which is removed from a lower portion of the second closed vessel to thereby provide the composition.

2. The process of claim 1 wherein the aldehyde is acetaldehyde.

3. The process of claim 1 wherein the lower alkanol transesterified fatty acid ester is a methyl ester derived from a methanol transesterification of a vegetable oil triglyceride.

4. The process of claim 1 wherein the aldehyde is acetaldehyde and the fatty acid ester is a methyl or ethyl ester derived from a methanol or ethanol transesterification of vegetable oil triglyceride and the reaction temperature is between about 80° C. and 200° C.

5. The process of any one of claims 1, 2, 3 or 4 wherein the acid catalyst is a resin acid catalyst.

6. The process of any one of claims 1, 2, 3 or 4 wherein the resin acid catalyst is an acidic resin or metal oxide.

7. The process of claim 1 wherein the mixture in steps (a) and (b) with fatty acid ester further comprises impurity amounts of free fatty acids and water.

8. A process for the preparation of a composition useful as a fuel oil which comprises reacting a mixture comprising 1,1-dimethoxyethane or 1,1-diethoxyethane with glycerol in a mixture comprising a lower alcohol transesterified fatty acid ester, wherein the alkanol contains 1 to 6 carbon atoms, in the presence of a solid acid catalyst in a closed vessel, at an elevated temperature to form a mixture of the fatty acid ester and a glycerol acetal to provide the composition.

9. The process of claim 8 further comprising a further prestep of reacting a mixture acetaldehyde and an ethyl- or methyl alcohol to form the 1,1-dimethoxyethane or 1,1-diethoxyethane and then removing water formed in the reaction from the mixture.

10. The process of claim 8 or 9 wherein methanol or ethanol are separated from the mixture.

11. The process of claim 8 or 9, wherein the reaction is conducted at a pressure between about 1 atmosphere and 27.2 atmosphere (400 psig) and at a temperature between about 80° and 200° C.

12. In a process for the preparation of a composition useful as a fuel from a transesterified fatty acid ester, the improvement which comprises:
   (a) reacting methanol or ethanol with acetaldehyde to form a 1,1-di-methoxyethane or 1,1-diethoxyethane and water in a reaction mixture;

(b) separating water from the reaction mixture; and
(c) reacting the reaction mixture of step (b) without the water with glycerol in a mixture comprising the transesterified fatty acid ester to form 2-methyl-4-hydroxymethyl 1,3-dioxolane in the transesterified fatty acid ester as the composition.

13. The process of claim 12 wherein the mole ratio of methanol or ethanol to acetaldehyde in step (a) is between about 1 to 1 and 4 to 1.

14. A continuous process for the preparation of a composition useful as a fuel oil which comprises:

reacting in a closed vessel a mixture comprising glycerol and a lower alkanol transesterified fatty acid ester, wherein the alkanol contains 1 to 6 carbon atoms, with an aldehyde, ketone containing 1 to 20 carbon atoms or a diether containing 2 to 20 carbon atoms below the second acid catalyst, in the presence of a solid acid catalyst in a closed vessel at an elevated temperature to form a mixture of the fatty acid ester and a glycerol acetal to provide the composition, wherein the ester is introduced above the catalyst and the alkanol and the aldehyde, ketone or diether is introduced below the catalyst to provide a countercurrent reaction on the catalyst.

15. The process of claim 14 wherein aldehyde is acetaldehyde.

* * * * *

UNITED STATES PATENT AND TRADEMARK OFFICE
CERTIFICATE OF CORRECTION

PATENT NO. : 7,321,052 B2  
APPLICATION NO. : 11/364241  
DATED : January 22, 2008  
INVENTOR(S) : Dennis J. Miller et al.

Page 1 of 1

It is certified that error appears in the above-identified patent and that said Letters Patent is hereby corrected as shown below:

Column 3, line 19, "800" should be --80--.

Column 4, line 2, "transestification" should be --transesterification--.

Signed and Sealed this

Third Day of June, 2008

JON W. DUDAS  
*Director of the United States Patent and Trademark Office*